(12) United States Patent
Li et al.

(10) Patent No.: US 12,251,463 B2
(45) Date of Patent: Mar. 18, 2025

(54) COMPOSITION CONTAINING WATER-SOLUBLE NON-IONIC POLYURETHANE DISPERSION, AND PREPARATION METHOD THEREFOR

(71) Applicant: WANHUA CHEMICAL GROUP CO., LTD., Shandong (CN)

(72) Inventors: Bangbang Li, Shandong (CN); Cao Zhou, Shandong (CN); Nuo Xu, Shandong (CN); Haidong Jia, Shandong (CN); Jie Zhang, Shandong (CN); Pengfei Qu, Shandong (CN); Jiakuan Sun, Shandong (CN)

(73) Assignee: WANHUA CHEMICAL GROUP CO., LTD., Shandong (CN)

(*) Notice: Subject to any disclaimer, the term of this patent is extended or adjusted under 35 U.S.C. 154(b) by 866 days.

(21) Appl. No.: 17/278,171

(22) PCT Filed: Dec. 11, 2018

(86) PCT No.: PCT/CN2018/120265
§ 371 (c)(1),
(2) Date: Mar. 19, 2021

(87) PCT Pub. No.: WO2020/113616
PCT Pub. Date: Jun. 11, 2020

(65) Prior Publication Data
US 2021/0346272 A1    Nov. 11, 2021

(30) Foreign Application Priority Data
Dec. 7, 2018   (CN) .......................... 201811491204.4

(51) Int. Cl.
| | | |
|---|---|---|
| *A61K 8/87* | (2006.01) | |
| *A61K 8/04* | (2006.01) | |
| *A61K 8/34* | (2006.01) | |
| *A61K 8/49* | (2006.01) | |
| *A61K 8/58* | (2006.01) | |
| *A61Q 5/00* | (2006.01) | |
| *A61Q 5/02* | (2006.01) | |
| *A61Q 5/12* | (2006.01) | |

(52) U.S. Cl.
CPC ................ *A61K 8/87* (2013.01); *A61K 8/044* (2013.01); *A61K 8/347* (2013.01); *A61K 8/4926* (2013.01); *A61K 8/4946* (2013.01); *A61K 8/58* (2013.01); *A61Q 5/006* (2013.01); *A61Q 5/02* (2013.01); *A61Q 5/12* (2013.01); *A61K 2800/48* (2013.01); *A61K 2800/524* (2013.01); *A61K 2800/5422* (2013.01)

(58) Field of Classification Search
None
See application file for complete search history.

(56) References Cited

U.S. PATENT DOCUMENTS

| | | |
|---|---|---|
| 2012/0247498 A1 | 10/2012 | Mathonneau |
| 2016/0067172 A1 | 3/2016 | Burch et al. |
| 2016/0101040 A1 | 4/2016 | D'Arras et al. |
| 2016/0120789 A1 | 5/2016 | D'Arras et al. |
| 2018/0022854 A1* | 1/2018 | Blaisdell ............. C08G 18/758 524/726 |

FOREIGN PATENT DOCUMENTS

| | | |
|---|---|---|
| CN | 1199754 A | 11/1998 |
| CN | 102020774 A | 4/2011 |
| CN | 102690404 A | 9/2012 |
| CN | 104031225 A | 9/2014 |
| CN | 105188851 A | 12/2015 |
| CN | 105622894 A | 6/2016 |
| CN | 106366281 A | 2/2017 |
| CN | 106714772 A | 5/2017 |
| CN | 107126378 A | 9/2017 |
| CN | 108546323 A | 9/2018 |
| EP | 0875557 A2 | 11/1998 |

OTHER PUBLICATIONS

International Search Report issued in PCT/CN2018/120265 on Aug. 22, 2019.
European Search Report issued Septemebr 15, 2022 in corresponding patent application EP 18941986.4-1109.
MINTEL Shampoo product information, (2014), http://www.gnpd.com, pp. 1-2.
Lepilleur, Carole: "Functional Polyurethanes for Personal Care Applications", An IP.com Prior Art Technical Disclosure, (2015), The Lubrizol Corp., pp. 1-70.

* cited by examiner

*Primary Examiner* — Nicole P Babson
(74) *Attorney, Agent, or Firm* — NORTON ROSE FULBRIGHT US LLP

(57) ABSTRACT

Provided is a composition containing water-soluble non-ionic polyurethane, comprising (a) 0.1-30 parts of water-soluble non-ionic polyurethane dispersions by weight; (b) 10-30 parts of decontaminating surfactants by weight; (c) 0.01-5 parts of conditioning agents by weight; and (d) 100 parts of aqueous carriers by weight. The composition in the present invention is used as shampoo, and can make hair naturally strong and extend the volumizing duration of hair.

18 Claims, No Drawings

COMPOSITION CONTAINING WATER-SOLUBLE NON-IONIC POLYURETHANE DISPERSION, AND PREPARATION METHOD THEREFOR

This application is a national phase under 35 U.S.C. § 371 of International Application No. PCT/CN2018/120265 filed Dec. 11, 2018, which claims the benefit of priority from Chinese Patent Application No. 201811491204.4 filed on Dec. 7, 2018. The entire contents of these applications are incorporated herein by reference in their entirety.

TECHNICAL FIELD

The present disclosure belongs to the field of cleaning and washing, and relates to a composition containing aqueous nonionic polyurethane.

BACKGROUND

As the standards of living continuously improve, people continue putting forward new demands for personal cleaning products. At present, a loss of hair, a lack of hair, and damaged hair have become primary concerns in the field of hair care. Shampoos are the simplest and most effective method to solve these problems.

A hair is mainly composed of the cuticle, cortex and medulla layers from the outside to the inside. The cuticle layer is formed by overlapping many small scales (i.e., hair scales). The cuticle layer is a protective layer. If the hair scales are arranged neatly, more light will be refracted and the hair will look bright and beautiful. If the hair scales are scratched or damaged, the hair will break easily and appear frizzy and dull. After the hair is dyed and permed, the water content of the hair scales will sharply decrease, so that the hair scales turn up and the hair has decreased comb performance and luster, which is also the main reason for the "stickiness" and brittleness of the damaged hair. Many of the existing commercially available shampoos for volumizing hairs increase the hair volume by opening the hair scales. However, this method for improving the softness of hairs tends to make the hairs drier and more difficult to comb. Moreover, the opened hair scales reflect light randomly, which will also reduce hair luster.

To solve the preceding problems, a patent document CN105188851A discloses a shampoo containing silicone grafted tapioca starch to provide the effect of hair volume gains. The silicone grafted tapioca starch particles can achieve smoothness without reducing the volume and be combined with a conditioner to achieve the effect of lifting hair roots. In essence, the patent document improves astringent hairs after the particles are added by using the conditioning property of silicone. However, though silicon compounds in the shampoo can make hairs smooth, these silicon-containing compounds are insoluble in water, very stable, and difficult to be biodegraded, so that silicon wrapped on the hairs and the scalp is not easy to be cleaned and will cause a certain burden on the hairs and the environment in the case of long-term use. Therefore, from the perspective of environmental protection and health, experts have suggested that the use of silicone oil in cosmetics should be reduced. Moreover, due to the introduction of silicone, the system has to introduce a silicone oil emulsification system, making it difficult for the shampoo to be transparent. A Chinese patent document CN107126378A discloses "the use of a surfactant composition and a detergent prepared from the same", in which anionic aqueous polyurethane is mainly used to provide a styling effect. However, volumizing and smoothing effects cannot be achieved. The detergent cannot be made transparent, which greatly restricts the acceptance of consumers, and the introduction of anionic resin in large amounts into the system with a cationic conditioner will greatly affect the stability of the system. A patent document CN102020774A discloses a moisture-permeable and waterproof aqueous PU resin for use in a fabric coating and mentions that the use of sulfonate can greatly improve the hydrophilicity of PUD to obtain good water-absorbing and moisturizing effects and be used in personal care products such as cosmetics and shampoos. However, the water-absorbing and moisturizing effects of PUD mentioned in the patent document reduce the volumizied hairs instead of providing a volumizing effect in shampoos.

SUMMARY

The problem to be solved by the present disclosure is to provide a nonionic polyurethane-based composition, which can achieve the effects of drying, smoothing and volumizing hairs by adding an aqueous nonionic polyurethane dispersion.

In a first aspect, the present disclosure provides a composition containing an aqueous nonionic polyurethane dispersion. The composition comprises:
- (a) 0.1 to 30 parts by weight of an aqueous nonionic polyurethane dispersion, preferably 5 to 25 parts by weight;
- (b) 10 to 30 parts by weight of a detersive surfactant, preferably 15 to 25 parts by weight;
- (c) 0.01 to 5 parts by weight of a conditioner, preferably 0.1 to 2 parts by weight; and
- (d) an aqueous carrier, the amount of which making the total weight of the composition to be 100 parts by weight; where
- (a) the aqueous nonionic polyurethane dispersion is a product comprising the following ingredients obtained through a reaction, which is preferably a conventional reaction at 70 to 80° C. and under normal pressure:
  S1: at least one diisocyanate, which is added in an amount of 5 to 25 wt %, preferably 9 to 13 wt %;
  S2: a macropolyol, which has a number average molecular weight of 500 to 3000 g/mol, preferably about 1000 to 2000 g/mol, and is added in an amount of 1 to 25 wt %, preferably 4 to 15 wt %;
  S3: at least one monohydric alcohol and/or diol containing a polyoxyethylene chain segment in a main chain and/or a side chain, which has a number average molecular weight of about 500 to 3000 g/mol and is added in an amount of 1 to 20 wt %, preferably 7 to 10 wt %;
  S4: at least one diol small-molecular chain extender containing active hydrogen, which has a molecular weight of 60 to 400 g/mol and is added in an amount of 0.1 to 10 wt %, preferably 1 to 5 wt %;
  S5: at least one diamine small-molecular chain extender containing active hydrogen, which has a molecular weight of 59 to 200 g/mol and is added in an amount of 0.01 to 5 wt %, preferably 0.04 to 0.7 wt %;
  S6: an organic solvent with a low boiling point, which is added in an amount of 0.2 to 2 times the total weight of $1 to S5, preferably 0.5 to 1.5 times;
  S7: distilled water, which is added in an amount of 20 to 80 wt %, preferably 57 to 70 wt %; and S8: a catalyst, which is added in an amount of 100 to 300 ppm of the total weight of S1 to S5.

The added amounts of each of the above ingredients are the contents relative to the total weight of the reaction system, where the total weight of the reaction system is a sum of weights of S1 to S5, S7, and S8 and equal to 100 wt %. S6 is a solvent removed off the final system.

Preferably, in the composition of the present disclosure, (a) the aqueous nonionic polyurethane dispersion is an aqueous nonionic polyurethane dispersion with a solids content of 20 wt % to 50 wt % and a particle size of 10 nm to 100 nm, preferably 10 nm to 60 nm.

Preferably, the diisocyanate in the ingredient S1 is one or more of toluene diisocyanate, diphenylmethane diisocyanate, isophorone diisocyanate, hexamethylene diisocyanate and dicyclohexylmethane diisocyanate, preferably, one or more of isophorone diisocyanate, hexamethylene diisocyanate and dicyclohexylmethane diisocyanate.

Preferably, the macropolyol in the ingredient S2 is one or more of polyethylene glycol, polypropylene glycol, polyethylene glycol-propylene glycol, polytetrahydrofuran ether glycol, polycaprolactone diol, polycarbonate diol, poly(ethylene glycol adipate) diol, poly(1,4-butylene glycol adipate) diol, poly(neopentyl glycol adipate) diol, poly(1,6-hexane glycol adipate) diol and poly(neopentyl glycol adipate-1,6-hexanediol) diol, preferably, polypropylene glycol.

Preferably, the monohydric alcohol and/or diol containing a polyoxyethylene chain segment in a main chain and/or a side chain in the ingredient S3 are preferably one or more of Tegomer® D-3403"poly(ethylene oxide) ether glycol with a hydroxyl value of 110 mgKOH/g, a number average molecular weight of about 1000 g/mol, and a functionality of 2 from the Perstorp Group, Sweden", Ymer™ N120 (poly(ethylene oxide) ether glycol with a hydroxyl value of 110 mgKOH/g, a number average molecular weight of about 1000 g/mol, and a functionality of 2 from the Perstorp Group, Sweden) produced by Perstrop and MPEG1200 (methoxypolyethylene glycol with a hydroxyl value of 165.4 mgKOH/g, a number average molecular weight of about 5000 g/mol, and a functionality of 2 from the South Korea's Lotte Group); more preferably, the ingredient S3 comprises Ymer™ N120 produced by Perstrop and/or MPEG1200 produced by South Korea's Lotte Group.

Preferably, the diol small-molecular chain extender containing active hydrogen in the ingredient S4 is one or more of 1,3-propanediol, 1,4-butanediol, diethylene glycol, neopentanediol, 1,6-hexanediol and 1,4-cyclohexanedimethanol, preferably, 1,4-cyclohexanedimethanol.

Preferably, the diamine small-molecular chain extender containing active hydrogen in the ingredient S5 is one or more of ethylene diamine, hexamethylene diamine, pentamethylene diamine, diethylene triamine, isophorone diamine, 4,4-diphenylmethane diamine and diethanolamine, preferably, one or two of ethylene diamine or isophorone diamine.

Preferably, the organic solvent with a low boiling point in the ingredient S6 includes, but is not limited to, acetone and/or butanone, preferably acetone.

Preferably, the catalyst in the ingredient S8 includes, but is not limited to, dibutyl tin dilaurate or organic bismuth 8108 produced by the Shepherd Chemical Company.

Preferably, in the aqueous nonionic polyurethane dispersion, the molar ratio R of the diisocyanate to the polyol is 1.85 to 4.5.

Preferably, in the aqueous nonionic polyurethane dispersion, the polyoxyethylene chain segment has a content of 20% or more of the weight of the solids of the aqueous nonionic polyurethane and is located on the end or a side group of the molecular chain.

In the composition of the present disclosure, (b) the detersive surfactant is selected from the group consisting of sodium laureth sulfate, alkyl ammonia oxide, alkyl betaine, cocamidopropyl betaine, disodium cocoamphodiacetate, alkyl sulfobetaine, alkyl glycinate, alkyl carboxy glycinate, alkyl amino propyl hydroxy, acyl taurate, acyl glutamate, sodium lauryl sulfate, sodium lauryl polyether sulfate, C12 to C16 alkyl glucoside, sodium lauroyl glutamate and mixtures thereof, where the alkyl group and the acyl group each have 8 to 19 carbon atoms. Preferably, the detersive surfactant is selected from the group consisting of sodium laureth sulfate, cocamidopropyl betaine, sodium lauryl sulfate, C12 to C16 alkyl glucoside, sodium lauroyl glutamate and mixtures thereof.

In the composition of the present disclosure, (c) the conditioner is selected from the group consisting of polyquaternary ammonium salts, quaternized proteins, cationic guar gums, water-soluble silicone oils and mixtures thereof. Preferably, the conditioner is selected from the group consisting of guar hydroxypropyltrimethylammonium chloride, polyquaternium-10, polydimethylsilicone and mixtures thereof.

In the composition of the present disclosure, (d) the aqueous carrier includes water and one selected from the group consisting of sodium chloride, a thickening agent, a pH regulator, an anti-dandruff agent, a fragrance, an emulsifier, a chelating agent, an opacifier, a preservative, a pearling agent, and mixtures thereof.

Preferably, the aqueous carrier includes one or more of:
0 to 2% by weight of sodium chloride;
0 to 3% by weight of a thickening agent;
0 to 1% by weight of a pH regulator;
0 to 3% by weight of an anti-dandruff agent;
0 to 3% by weight of a fragrance;
0 to 3% by weight of an emulsifier;
0 to 0.5% by weight of a chelating agent;
0 to 1% by weight of an opacifier;
0 to 1% by weight of a preservative; and
0 to 1% by weight of a pearling agent.

Further, the thickening agent is selected from the group consisting of sodium chloride, cocamide MIPA, PEG-150 distearate, ammonium chloride, hydroxyethyl cellulose, hydroxypropyl methyl cellulose, polyacrylic acid, polyacrylate, polyurethane and polyoxyethylene with a high molecular weight, preferably sodium chloride.

The anti-dandruff agent is selected from the group consisting of climbazole, zinc pyrithione, piroctone ethanolamine and triclosan, preferably piroctone ethanolamine.

The preservative is selected from the group consisting of casson, paraben, sodium benzoate, salicylic acid, DMDM hydantoin and phenoxyethanol, preferably sodium benzoate.

The fragrance is an artificial or natural fragrance, preferably a natural fragrance.

Preferably, the composition is used as a shampoo.

In a second aspect, the present disclosure provides a method for preparing the composition. The method includes: stirring and mixing ingredients according to proportions thereof to a uniform state; preferably, heating, cooling, vacuum or other manners may be used.

In the present disclosure, the particle size of the aqueous nonionic polyurethane dispersion, the molar ratio (R) of the isocyanate to the polyol in the final product, and the content of the polyoxyethylene chain segment are designed, causing good film elasticity, high glossiness, good toughness, moderate hardness and an unsticky feeling. The polyoxyethylene chain segment has a weight of 20% or more of the solids content of the aqueous nonionic polyurethane dispersion and is located on the end or a side group of the molecular chain, so that polyurethane microspheres can be well dispersed in water, and polyurethane can form an unsticky protective film on the surface of a hair. Due to a nonionic hydrophilic chain segment, the aqueous nonionic polyurethane not only has good compatibility with nonionic surfactants, thickening agents and silicone oil but also has good compatibility with various common anionic and zwitterionic surfactants, cationic conditioners, sodium chloride, hydrolyzed protein nutrients and alkali-swellable thickening systems compared with anionic polyurethane, so that the system has better stability. When added to other ingredients, the system can not only ensure the transparency of the shampoo but also form hydrogen bonds between nonionic groups and the keratin of the hair after use, which is conducive to the attachment to the hair to form a film, achieving strong roots, increasing the volume of the hair. Commercially available shampoos generally improve the smoothness of the hair by adding cationic conditioners. The shampoos added with anionic polyurethane will greatly reduce the deposition effect of the cationic conditioners due to the electrostatic effect of the cationic conditioners, which will affect the conditioning performance of the hair after use. Moreover, the nonionic polyurethane forms a film on the hair, and the film can shield part of electric charges and reduce the mass of hair due to static electricity, so that the hair is easier to comb.

After added to a shampoo formulation, the nonionic polyurethane dispersion with a particle size of 10 nm to 100 nm, especially 10 nm to 60 nm, neither changes the transmittance of the shampoo nor affects the solubility of the surfactant, so that the formulation can still be maintained transparent, thereby greatly improving the acceptance of consumers. Due to a dyeing and perming process or a long-term exposure to ultraviolet rays, hair scales are prone to turn up due to a lack of water and thus damaged to form voids, which reduces the smoothness of the hair. A long-term failure to effectively improve the damaged hair scales will cause flabby hairs and a decrease in hair volume. Polyurethane particles within this range of particle size can more easily be filled in the voids of the damaged hair, which can not only improves hair luster but also make it easier for polyurethane to form a film on the hair, increasing the hair volume, achieving strong roots, increasing spaces between hairs, and volumizing the hairs. The nonionic polyurethane with small particle size enters the voids of the hair, fits the damaged hair scales to be filled in the voids, blocks dirt and reduces the difficulty of combing. The hydrogen bonding of nonionic and water molecules can maintain moisture in the hair and repair the damaged hair. The special design avoids stickiness after polyurethane forms a film outside the hair scales and finally improves the smoothness of the hair.

The composition of the present disclosure has the advantages of dry film formation, non-stickiness, high glossiness, good toughness and good elasticity. The non-ions form hydrogen bonds with the keratin in the hair and are easy to be attached to the damaged hair scales of the hair and be filled in the voids of the hair; and the nonionic polyurethane is also easy to form a film on the hair and increase the hair volume and achieves strong hair roots and increases the spaces between hairs after use, thereby volumizing hairs and improving soft and flabby hairs. In the composition of the present disclosure, the ratio of isocyanate to polyol is moderate, so that the composition has an appropriate glass transition temperature. After the nonionic polyurethane forms a film on the surface of the hair, the film is neither sticky (improving the smoothness of the hair) nor too hard (so that the hair is not styled hard and volumized naturally), which can make hairs naturally strong and extend the volumizing duration of hair.

DETAILED DESCRIPTION

Raw materials used in examples and comparative examples:
WANNATE®IPDI (isophorone diisocyanate with a content of NCO (the mass of NCO groups/the total molecular mass) being about 37.8% from Wanhua Chemical Group Co., Ltd.);
WANNATE®HMDI (dicyclohexylmethane diisocyanate with a content of NCO being about 32.0% from Wanhua Chemical Group Co., Ltd.);
Ymer™ N120;
CMA-654 (polyneopentanediol adipate-hexanediol diol with a hydroxyl value of 74.8 mgKOH/g, a number average molecular weight of about 1500 g/mol, and a functionality of 2 from HuaDa Chemical Group Co., Ltd, Yantai);
WANNATE®HDI (hexamethylene diisocyanate with a content of NCO being about 50.0% from Wanhua Chemical Group Co., Ltd.);
VESTAMIN®A95 (sodium 2-[(2-aminoethyl)amino]ethanesulphonate which is an aqueous solution with a solids content of 51±2% and has an amine value of 260±20 mgKOH/g from EVONIK, Germany);
CHDM (1,4-cyclohexanedimethanol from Kellin Chemicals Co., Ltd.);
NPG (neopentyl glycol from Wanhua Chemical Group Co., Ltd.);
EDA (ethylenediamine from BASF, Germany);
8108: an organic bismuth catalyst (from the Shepherd Chemical Company);
PPG1000 (polypropylene glycol from Shandong Bluestar Dongda Co., Ltd.);
IPDA (isophorone diamine from Wanhua Chemical Group Co., Ltd.);
Sodium laureth sulfate (an anionic surfactant from Shandong Baiqian Chemical Co., Ltd.);
C12 to C16 alkyl glucoside (a nonionic surfactant from Sinolight Surfactants Technology Co., Ltd.);
Sodium lauroyl glutamate (an amphoteric surfactant from Wuhan Easy Diagnosis Biomedicine Co., Ltd.);
Guar hydroxypropyltrimethylammonium chloride (a cationic guar gum conditioner from Guangzhou Tinci High-Tech Material Co., Ltd.);
Polyquaternium-10 (polyquaternium conditioner from Guangzhou Tinci High-Tech Material Co., Ltd.);
Polydimethylsilicone (a water-soluble silicone oil from Guangzhou Tinci High-Tech Material Co., Ltd.);
Polyacrylic acid polymer (a thickening agent from Lubrizol);
Citric acid (a pH regulator from Guangzhou Huazhiwang Chemical Co., Ltd.);
Zinc pyrithione (an anti-dandruff agent from Jining Baiyi Chemical Co., Ltd.);
Piroctone ethanolamine salt (an anti-dandruff agent from Shandong Baiqian Chemical Co., Ltd.);
Ammonium lauryl sulfate (an emulsifier from Henan Boteer Chemical Products Co., Ltd.);
Disodium EDTA (a chelating agent from AkzoNobel, USA);
Styrene/acrylate copolymer (an opacifier from Dow Chemical);
Phenoxyethanol (a preservative from Dow Chemical);

Ethylene glycol distearate and fatty alcohol ether sodium sulfate (a pearling agent from Jining Baiyi Chemical Co., Ltd.);

TCW2890404 (a fragrance from City Flower Flavors & Fragrances Ltd.).

Anionic Polyurethane

CMA-654 (from HuaDa Chemical Group Co., Ltd, Yantai) (80 g) and neopentyl glycol (2.5 g) were added to a four-necked flask, mixed and stirred for 10 min at 70° C., and cooled to 50° C. WANNATE®HDI (19 g) was added and reacted with the mixture. The reaction was tested, and when NCO % approximates 2.95 wt %, the prepolymer was cooled to 40° C. and dissolved in 150 g of acetone solvent. The prepolymer and the acetone solvent were mixed for 15 min, added with a solution of ethylene diamine (0.7 g) and VESTAMIN®A95 (5 g) in 15 g of deionized water, and reacted at 45° C. for 30 min. 210 g of water was added under a shear dispersion condition and then distilled under reduced pressure to remove acetone to obtain a polyurethane dispersion with a solids content of about 31 wt % and a particle size of 50 nm. (R=2.12, and there was no ethylene oxide chain segment).

Nonionic Polyurethane Dispersion-1

WANNATE®IPDI (S1) (87 g), PPG1000 (S2) (31 g), CHDM (S4) (29 g), Ymer™ N120 (S3) (65 g), 8108 (S8) (0.0424 g) and acetone (S6) (21.2 g) were added to a four-necked flask equipped with a stirring rod and a thermometer, heated to 70° C., reacted until NCO reached 3.0% (a theoretical NCO value was 3.39%), and cooled to 40° C. The reaction solution was added with 212 g of acetone (S6) and then added with 487 g of distilled water (S7) when stirred at a high speed (1200 to 1500 r/min). After the reaction solution was dispersed, 4.2 g of EDA (S5) and 17 g of distilled water (S7) were added and stirred for 5 min to remove acetone and obtain a nonionic polyurethane dispersion-1 with a particle size of 26 nm and a solids content of 30 wt %. R=4.08, and polyoxyethylene chain segments account for 30% of the solids by weight.

Nonionic Polyurethane Dispersion-2

WANNATE®IPDI (S1) (90 g), PPG1000 (S2) (102 g), CHDM (S4) (21 g), Ymer™ N120 (S3) (60 g), 8108 (S8) (0.05 g) and acetone (S6) (27.3 g) were added to a four-necked flask equipped with a stirring rod and a thermometer, heated to 70° C., reacted until NCO reached 2.3% (a theoretical NCO value was 2.70%), and cooled to 35° C. The reaction solution was added with 273 g of acetone (S6) and then added with 538 g of water (S7) when stirred at a high speed (1200 to 1500 r/min). After the reaction solution was dispersed, 4 g of EDA (S5) and 16 g of water (S7) were added and stirred for 5 min to remove acetone and obtain a nonionic polyurethane dispersion-2 with a particle size of 36 nm and a solids content of 30%. R=2.50, and polyoxyethylene chain segments account for 21.6% of the solids by weight.

Nonionic Polyurethane Dispersion-3

WANNATE®IPDI (S1) (63 g), PPG1000 (S2) (102 g), CHDM (S4) (9 g), Ymer™ N120 (S3) (50 g), 8108 (S8) (0.04 g) and acetone (S6) (22.4 g) were added to a four-necked flask equipped with a stirring rod and a thermometer, heated to 70° C., reacted until NCO reached 2.1% (a theoretical NCO value was 2.33%), and cooled to 35° C. The reaction solution was added with 224 g of acetone (S6) and then added with 442 g of water (S7) when stirred at a high speed (1200 to 1500 r/min). After the reaction solution was dispersed, 3 g of EDA (S5) and 12 g of water (S7) were added and stirred for 5 min to remove acetone and obtain a nonionic polyurethane dispersion-3 with a particle size of 20 nm and a solids content of 30%. R=1.87, and polyoxyethylene chain segments account for 22.0% of the solids by weight.

Example 1

The formulations are shown in the following table (parts by weight). A preparation method includes: preparing ingredients according to their proportions, sequentially adding the ingredients when stirring at 1500 r/min and room temperature, adjusting a PH value to 5 to 6, and stirring the ingredients for 15 to 30 min until they are completely dispersed.

| Raw Materials | Example 1 | Example 2 | Example 3 | Comparative Example 1 | Comparative Example 2 | Comparative Example 3 | Comparative Example 4 |
|---|---|---|---|---|---|---|---|
| Nonionic polyurethane dispersion-1 | 15 | 0 | 0 | 0 | 0 | 0 | 0 |
| Nonionic polyurethane dispersion-2 | 0 | 10 | 0 | 0 | 0 | 0 | 0 |
| Nonionic polyurethane dispersion-3 | 0 | 0 | 20 | 0 | 0 | 0 | 0 |
| Anionic polyurethane dispersion | 0 | 0 | 0 | 0 | 0 | 0 | 20 |
| Sodium laureth sulfate | 14 | 14 | 14 | 14 | 14 | 14 | 14 |
| Cocamidopropyl betaine | 3 | 3 | 3 | 3 | 3 | 3 | 3 |
| Guar hydroxypropyltrimethyl ammonium chloride | 0 | 0.3 | 0 | 0 | 0.3 | 0 | 0 |
| Polydimethylsilicone | 0 | 0 | 0 | 0 | 0 | 1 | 0 |
| Polyquaternium-10 | 0.4 | 0.4 | 0.4 | 0.4 | 0.4 | 0.4 | 0.4 |
| Fragrance | 0.5 | 0.5 | 0.5 | 0.5 | 0.5 | 0.5 | 0.5 |
| Sodium benzoate | 0.5 | 0.5 | 0.5 | 0.5 | 0.5 | 0.5 | 0.5 |
| Salicylic acid | 0.2 | 0.2 | 0.2 | 0.2 | 0.2 | 0.2 | 0.2 |
| Sodium chloride | 0.5 | 0.5 | 0.5 | 0.5 | 0.5 | 0.5 | 0.5 |
| Piroctone ethanolamine salt | 0.2 | 0.2 | 0.2 | 0.2 | 0.2 | 0.2 | 0.2 |
| Deionized water | Making the total weight of the composition to be 100 | Making the total weight of the composition to be 100 | Making the total weight of the composition to be 100 | Making the total weight of the composition to be 100 | Making the total weight of the composition to be 100 | Making the total weight of the composition to be 100 | Making the total weight of the composition to be 100 |

Test Method

A. Hair Tress Test In Vitro

A sodium laureth sulfate solution of 15 wt % was used for cleaning unused hairs. After the hairs were dried, a DIA STRON MTT175 hair tester was used for testing compression work to pull a hair stress by 15 cm at a 1 cm hole as an initial work of tensile force which was recorded as $W_{initial}$. The compositions in the preceding examples and comparative examples (0.6 g) were used for cleaning the hair tress, and a MTT175 hair tester was used and the above test steps were repeated to obtain the test work of tensile force, which was recorded as $W_{test}$. A difference between the test work of tensile force and the initial work of tensile force was recorded as $W_{treatment}=W_{test}-W_{initial}$. A difference between the test work of tensile force and the initial work of tensile force for a commercially available brand of transparent volumizing shampoo was used as top control ($W_{topcontrol}$), and a difference between the test work of tensile force and the initial work of tensile force for a blank shampoo (no polymer) was used as bottom control ($W_{bottomcontrol}$). A volume index of the tested composition may be expressed as:

then evaluated the shampoos (from 1 to 5), where 1 represents soft hairs without a volumized effect, and 5 represents good hair volumizing.

Smoothness test: 10 women with thin and soft hairs were recruited to clean hairs once every two days for 2 weeks and then evaluated the shampoos (from 1 to 5), where 1 represents serious tangling, difficult combing and very large combing resistance of dry hairs, and 5 represents no tangling, easy combing and almost no resistance.

Dandruff: 10 women with thin and soft hairs were recruited to clean hairs once every two days for 2 weeks and then evaluated the shampoos (from 1 to 5), where 1 represents serious dandruff, and 5 represents almost no dandruff.

Shampoo appearance: the transparency in appearance of the shampoo was scored and evaluated (from 1 to 5), where 1 represents a lowest degree to which the transparency in appearance of the shampoo was accepted, and 5 represents a highest degree to which the transparency in appearance of the shampoo was accepted.

Evaluation Results:

|  | Hair Tress Test in Vitro (%) | | Sensory Evaluation of Consumers (1 to 5) | | | |
| --- | --- | --- | --- | --- | --- | --- |
| Evaluation Item | VolumeIndex | Smoothness Index | Volumizing | Smoothness | Dandruff | Shampoo Appearance |
| Example 1 | 120 | 96 | 5 | 5 | 5 | 5 |
| Example 2 | 101 | 92 | 4 | 5 | 5 | 5 |
| Example 3 | 130 | 98 | 5 | 5 | 5 | 4 |
| Comparative Example 1 | 0 | 78 | 1 | 3 | 5 | 5 |
| Comparative Example 2 | 8 | 80 | 1 | 4 | 5 | 5 |
| Comparative Example 3 | 5 | 85 | 1 | 4 | 5 | 1 |
| Comparative Example 4 | 103 | 77 | 4 | 3 | 5 | 2 |
| Commercially available brand of transparent volumizing shampoo | 100 | 60 | 4 | 2 | 5 | 5 |

$$\text{Volume index} = 100\% \times \frac{W_{treatment} - W_{bottomcontrol}}{W_{topcontrol} - W_{bottomcontrol}} \bigg/ (W_{topcontrol} - W_{bottomcontrol})$$

Hair tress smoothness test: A sodium laureth sulfate solution of 15 wt % was used for cleaning two groups of unused hair tresses. The preceding MTT175 hair tester was used for obtaining combing work as an initial combing work which was recorded as $W_{initial1}$ and $W_{initial2}$. The hair tresses were cleaned with a test shampoo (containing a polymer) and a blank shampoo (without any conditioner) which were diluted twenty times. Test combing work and blank combing work were obtained through the above test steps and recorded as $W_{test}$ and $W_{blank}$, respectively. A dry hair combing smoothness index may be recorded as:

Smoothness index=$(W_{blank}/W_{initial2}-W_{test}/W_{initial1})*100\%$.

B. Experiments for Sensory Evaluation of Consumers

Volumizing test: 10 women with thin and soft hairs were recruited to clean hairs once every two days for 2 weeks and It can be seen from the evaluation results that Example 1, Example 2 and Example 3 have relatively excellent volumizing effect, good smoothness and good appearances and are not prone to dandruff from the aspects of hair tress and consumer evaluation.

What is claimed is:

1. A composition containing an aqueous nonionic polyurethane dispersion, comprising:
    (a) 0.1 to 30 parts by weight of an aqueous nonionic polyurethane dispersion;
    (b) 10 to 30 parts by weight of a detersive surfactant;
    (c) 0.01 to 5 parts by weight of a conditioner; and
    (d) an aqueous carrier, the amount of which making the total weight of the composition to be 100 parts by weight;
    wherein (a) the aqueous nonionic polyurethane dispersion is an aqueous nonionic polyurethane dispersion with a solids content of 20 wt % to 50 wt % and a particle size of 10 nm to 100 nm;
    wherein raw materials for preparing (a) the aqueous nonionic polyurethane dispersion comprise the following ingredients:

S1: at least one diisocyanate, which is added in an amount of 5 to 25 wt %;

S2: a macropolyol, which has a number average molecular weight of 500 to 3000 g/mol, and is added in an amount of 1 to 25 wt %;

S3: at least one monohydric alcohol and/or diol containing a polyoxyethylene chain segment in a main chain and/or a side chain, which has a number average molecular weight of 500 to 3000 g/mol and is added in an amount of 1 to 20 wt %;

S4: at least one diol small-molecular chain extender containing active hydrogen, which has a molecular weight of 60 to 400 g/mol and is added in an amount of 0.1 to 10 wt %;

S5: at least one diamine small-molecular chain extender containing active hydrogen, which has a molecular weight of 59 to 200 g/mol and is added in an amount of 0.01 to 5 wt %;

S6: an organic solvent, which is added in an amount of 0.2 to 2 times the total weight of S1 to S5;

S7: distilled water, which is added in an amount of 20 to 80 wt %; and

S8: a catalyst, which is added in an amount of 100 to 300 ppm of the total weight of S1 to S5; wherein the added amounts of each of the above ingredients are the contents relative to the total weight of the reaction system, where the total weight of the reaction system is a sum of weights of S1 to S5, S7, and S8 and equal to 100 wt %;

in the aqueous nonionic polyurethane dispersion, the molar ratio R of the at least one diisocyanate to the macropolyol is 1.85 to 4.5.

2. The composition according to claim 1, wherein raw materials for preparing (a) the aqueous nonionic polyurethane dispersion comprise the following ingredients:

S1: at least one diisocyanate, which is added in an amount of 5 to 25 wt %;

S2: a macropolyol, which has a number average molecular weight of 1000 to 2000 g/mol, and is added in an amount of 1 to 25 wt %;

S3: at least one monohydric alcohol and/or diol containing a polyoxyethylene chain segment in a main chain and/or a side chain, which has a number average molecular weight of 500 to 3000 g/mol and is added in an amount of 1 to 20 wt %;

S4: at least one diol small-molecular chain extender containing active hydrogen, which has a molecular weight of 60 to 400 g/mol and is added in an amount of 0.1 to 10 wt %;

S5: at least one diamine small-molecular chain extender containing active hydrogen, which has a molecular weight of 59 to 200 g/mol and is added in an amount of 0.01 to 5 wt %;

S6: an organic solvent, which is added in an amount of 0.2 to 2 times the total weight of S1 to S5;

S7: distilled water, which is added in an amount of 20 to 80 wt %; and

S8: a catalyst, which is added in an amount of 100 to 300 ppm of the total weight of S1 to S5; wherein the added amounts of each of the above ingredients are the contents relative to the total weight of the reaction system, where the total weight of the reaction system is a sum of weights of S1 to S5, S7, and S8 and equal to 100 wt %.

3. The composition according to claim 1, wherein (b) the detersive surfactant is selected from the group consisting of sodium laureth sulfate, alkyl ammonia oxide, alkyl betaine, cocamidopropyl betaine, disodium cocoamphodiacetate, alkyl sulfobetaine, alkyl glycinate, alkyl carboxy glycinate, alkyl amino propyl hydroxy, acyl taurate, acyl glutamate, sodium lauryl sulfate, sodium lauryl polyether sulfate, C12 to C16 alkyl glucoside, sodium lauroyl glutamate and mixtures thereof, wherein the alkyl groups and the acyl groups each have 8 to 19 carbon atoms.

4. The composition according to claim 1, wherein (c) the conditioner is selected from the group consisting of polyquaternary ammonium salts, quaternized proteins, cationic guar gums, water-soluble silicone oils and mixtures thereof.

5. The composition according to claim 1, wherein (d) the aqueous carrier comprises water and one selected from the group consisting of sodium chloride, a thickening agent, a pH regulator, an anti-dandruff agent, a fragrance, an emulsifier, a chelating agent, an opacifier, a preservative, a pearling agent, and mixtures thereof.

6. The composition according to claim 5, wherein the thickening agent is selected from the group consisting of sodium chloride, cocamide MIPA, PEG-150 distearate, ammonium chloride, hydroxyethyl cellulose, hydroxypropyl methyl cellulose, polyacrylic acid, polyacrylate, polyurethane and polyoxyethylene with a high molecular weight;

the anti-dandruff agent is selected from the group consisting of climbazole, zinc pyrithione, piroctone ethanolamine and triclosan;

the preservative is selected from the group consisting of casson, paraben, sodium benzoate, salicylic acid, DMDM hydantoin and phenoxyethanol; and the fragrance is an artificial or natural fragrance.

7. The composition according to claim 1, wherein the composition is a shampoo.

8. The composition according to claim 2, wherein the at least one diisocyanate in the ingredient S1 is selected from the group consisting of toluene diisocyanate, diphenylmethane diisocyanate, isophorone diisocyanate, hexamethylene diisocyanate and dicyclohexylmethane diisocyanate.

9. The composition according to claim 2, wherein the macropolyol in the ingredient S2 is one or more of polyethylene glycol, polypropylene glycol, polyethylene glycol-propylene glycol, polytetrahydrofuran ether glycol, polycaprolactone diol, polycarbonate diol, poly(ethylene glycol adipate) diol, poly(1,4-butylene glycol adipate) diol, poly(neopentyl glycol adipate) diol, poly(1,6-hexane glycol adipate) diol and poly(neopentyl glycol adipate-1,6-hexane glycol) diol.

10. The composition according to claim 2, wherein the at least one monohydric alcohol and/or diol containing a polyoxyethylene chain segment in a main chain and/or a side chain in the ingredient S3 is poly(ethylene oxide) ether glycol.

11. The composition according to claim 2, wherein the at least one diol small-molecular chain extender containing active hydrogen in the ingredient S4 is one or more of 1,3-propanediol, 1,4-butanediol, diethylene glycol, neopentanediol, 1,6-hexanediol and 1,4-cyclohexanedimethanol.

12. The composition according to claim 2, wherein the at least one diamine small-molecular chain extender containing active hydrogen in the ingredient S5 is one or more of ethylene diamine, hexamethylene diamine, pentamethylene diamine, diethylene triamine, isophorone diamine, 4,4-diphenylmethane diamine and diethanolamine.

13. The composition according to claim 2, wherein the organic solvent in the ingredient S6 comprises acetone and/or butanone.

14. The composition according to claim 2, wherein the catalyst in the ingredient S8 comprises dibutyl tin dilaurate.

15. The composition according to claim 2, wherein in the aqueous nonionic polyurethane dispersion, the polyoxyethylene chain segment has a content of 20% or more of the weight of the solids of the aqueous nonionic polyurethane and is located on the end or a side group of the molecular chain.

16. The composition according to claim 4, wherein the conditioner is selected from the group consisting of guar hydroxypropyltrimethylammonium chloride, polyquaternium-10, polydimethylsilicone and mixtures thereof.

17. The composition according to claim 5, wherein the aqueous carrier comprises one or more of:
0 to 2% by weight of sodium chloride;
0 to 3% by weight of a thickening agent;
0 to 1% by weight of a pH regulator;
0 to 3% by weight of an anti-dandruff agent;
0 to 3% by weight of a fragrance;
0 to 3% by weight of an emulsifier;
0 to 0.5% by weight of a chelating agent;
0 to 1% by weight of an opacifier;
0 to 1% by weight of a preservative; and
0 to 1% by weight of a pearling agent.

18. A method for preparing the composition according to claim 1, comprising: stirring and mixing ingredients according to proportions thereof to a uniform state.

\* \* \* \* \*